United States Patent [19]

Patchornik et al.

[11] Patent Number: 4,552,922
[45] Date of Patent: Nov. 12, 1985

[54] METHOD FOR MULTIPOLYMER SYNTHESIS OF ORGANIC COMPOUNDS

[75] Inventors: Abraham Patchornik, Ness Ziona; Yechiel Shai, Yehud; Shimeon Pass, Kiryat ONO, all of Israel

[73] Assignee: Yeda Research & Development Co. Ltd., Rehovot, Israel

[21] Appl. No.: 507,443

[22] Filed: Jun. 24, 1983

Related U.S. Application Data

[63] Continuation-in-part of Ser. No. 506,862, Oct. 22, 1983, abandoned.

[30] Foreign Application Priority Data

Jun. 22, 1982 [IL] Israel ..................................... 66094

[51] Int. Cl.$^4$ .................... C08L 89/00; C07C 103/52; C07H 15/12
[52] U.S. Cl. ......................... 525/54.11; 260/112.5 R; 525/54.1; 536/27; 536/28; 536/29
[58] Field of Search ........................... 525/54.1, 54.11; 536/27, 28, 29; 260/112.5 R

[56] References Cited

U.S. PATENT DOCUMENTS

| | | | |
|---|---|---|---|
| 4,065,412 | 12/1977 | Dreyer ............................... | 525/54.1 |
| 4,115,305 | 9/1978 | Hornby et al. ...................... | 525/54.1 |
| 4,119,589 | 10/1978 | Horn et al. ......................... | 525/54.1 |
| 4,483,964 | 11/1984 | Urdea et al. ....................... | 525/54.11 |

OTHER PUBLICATIONS

Rebek, Jr. J., "Mechanistic Studies Using Solid Support: the Three-Phase Test", *Tetrahedron* vol. 35, pp. 723-731, Pergamon Press, Ltd., 1979.
Akelah, A. et al, "Application of Functionalized Polymers in Organic Synthesis" *Chem. Rev.*, 1981, 81: 557-587.
Mathur, N. K. et al, "Functionalization of Styrene-- Based Polymers via Choromethylation and other method " *Polymers as Aids in Organic Chemistry*, pp. 18-36.
Kraus, M. A. et al, "Polymeric Reagents" *Macromol. Rev.* vol. 15, pp. 55-105.
Cohen, B. J. et al, "Wolf and Lamb" Reactions:Equilibrium and Kinetic Effects in Multipolymer Systems" *J. Am. Chem. Soc.* 1981, 103, 7620-7629.
Cohen B. J. et al, "Organic Synthesis Involving Multipolymer Reactions, Polymeric Trityllithium", *J. Am. Chem. Soc.* 1977, 99:12 pp. 4165-4166.
Patchornick, A., "Some Novel Developments in the Use of Polymeric Reagents Multiphase and Multistep Reactions", *Nouv. J. Chim.* 6, 12, 639-43, 1982.
Journal of the American Chem. Soc. 97, (1975), 454-456.
Chem. Abstr. 87, (1977) 98467b.
Chem. Abstr. 84, (1976) 165450u.
Chem. Abstr. 85, (1976) 89499v.

*Primary Examiner*—Delbert R. Phillips
*Attorney, Agent, or Firm*—Browdy and Neimark

[57] ABSTRACT

A broad range of organic synthesis reactions can be conducted by means of a process using two polymeric supports, each carrying different reactive species. A liquid medium containing a specifically selected intermediate reactant, in a solvent, is circulated between the supports in order to remove the reactive species from the first support by reaction with the intermediate, and permit the reactive species thus removed to react with the reactive species of the second support, at the same time regenerating the original intermediate reactant. This circulation continues until the second support is suitably loaded with the reaction product, at which time the circulation is stopped and the reaction products separated and recovered. The process may be carried out in an automated apparatus in which sensors are placed at the entrance and exit of the column carrying the second polymeric support. The sensors are capable of sensing the relative presence of the intermediate reactant. When the same content of intermediate reactant is sensed at both the entrance and exit of the second column, the circulation will be automatically stopped as this will indicate complete loading of the second column.

23 Claims, 4 Drawing Figures

METHOD FOR MULTIPOLYMER SYNTHESIS OF ORGANIC COMPOUNDS

CROSS REFERENCE TO RELATED APPLICATIONS

The present application is continuation-in-part of application Ser. No. 506,862, filed June 22, 1983, now abandoned, the entire contents of which are hereby incorporated by reference.

FIELD OF THE INVENTION

The present invention relates to a process and apparatus for effecting chemical reactions. The process and apparatus are based on the synthesis of chemical compounds by means of certain reactive species which are transferred from a solid polymeric support (which may be in column form) to another polymeric support (which may also be in column form). This novel process and apparatus for carrying out chemical reactions is of very versatile applicability and can be used for the selective and high yield synthesis of various types of compounds with self monitoring.

BACKGROUND OF THE INVENTION

The use of carrier-bound reactive species for analytical purposes is known. Rebek et al, *JACS* 97:2 (1975) page 454 and Rebek et al, *Tetrahedron* vol. 35, pages 723–737, 1979 described a three phase test for the detection of intermediates. The test involves the generation of a reactive intermediate from an insoluble polymeric precursor and its detection by trapping on a second solid phase. This method is especially useful for the detection of intermediates in nucleophilic catalysis. The same principle was applied by Rebek to reactions involving metaphosphates, cyclobutadiene and in phosphate transfer reactions. Except for certain specific acylation reactions, none of the three-phase reactions of Rebek disclose regenerable intermediates. Although similar in principle to the reaction carried out in the device of the present invention, Rebek et al describes an analytical reaction with minimum quantities of reactants without envisaging applicability for synthetic purposes. Moreover, in the case of Rebek, the two polymers were mixed together or were separated by sintered glass frit and the reactive intermediate formed was transferred from one polymer to the other. This system does not permit monitoring and automation of the reaction.

SUMMARY OF THE INVENTION

Accordingly, it is an object of the present invention to provide a broadly applicable method of synthesis of organic compounds.

It is another object of the present invention to provide an apparatus for the automatic synthesis and recovery of organic compounds.

These and other objects of the present invention are attained through the use of first and second polymeric supports each carrying different reactive species. A liquid medium containing a specifically selected intermediate reactant, in a solvent, is circulated between the supports in order to remove the reactive species from the first support by reaction with the intermediate, and permit the reactive species thus removed to react with the reactive species of the second support, at the same time regenerating the original intermediate reactant. This circulation continues until the second support is suitably loaded with the reaction product, at which time the circulation of the intermediate reactant is stopped and the reaction product separated and recovered from the second support. The obtained reaction product will be free of the original reactant from the first support and the intermediate reactants, thus permitting selective and high yield synthesis.

The initial reaction product on the second polymeric support may itself be used as a new reactive species, without separating it from the polymeric support. A new first polymeric support/reactive species can be substituted for the original first polymeric support to add another moiety to the new reactive species on the second support. In this way longer chain products, as, for example, polypeptides or polynucleotides may be synthesized by the method of the present invention.

The process of the present invention is preferably carried out in an apparatus which permits automation of the process. In this apparatus the two polymeric supports are each placed into respective columns between which the intermediate reactant may circulate. Two sensors capable of sensing the relative presence of the intermediate reactant are placed respectively at the entrance and exit of the second polymeric column. When the same content of intermediate reactant is sensed at both the entrance and exit of the second column, this will indicate completion of loading of the second column and the begining of the next synthesis phase or the separation and recovery phase. A microcomputer is provided to react to this indication of completion by closing of appropriate valves to permit completion of the process. The sensors may be capable of quantitative analysis of the concentration of the intermediate reactant, thus providing a continuous direct record of yield.

BRIEF DESCRIPTION OF THE DRAWINGS

The present invention will be better understood upon consideration of the following detailed description in conjunction with the attached drawings, in which.

DETAILED DESCRIPTION OF PREFERRED EMBODIMENTS

The process of the present invention is applicable for the synthesis of any organic compound B-A which is conventionally synthesizable by the reaction $$B + \alpha\text{—}A \rightarrow B\text{—}A + \alpha \qquad (I).$$

In the present process, however, B is bound by a chemical bond to a reactive polymer , usually by means of a linking moiety L, and A is bound by a chemical bond to a reactive polymer P by means of a linking moiety $\alpha'$. Intermediate reactant $\alpha$, capable of reacting with $\textcircled{P}$—$\alpha'$—A to form $\alpha$—A, is fed to the polymer on which $\alpha'$—A is bound (the first column) to form the intermediate compound $\alpha$—A which is then circulated to the polymer on which B is bound (the second column) where it reacts with (P')—L—B to form (P')—L—B—A and the original intermediate reactant α. The regenerated original α is then circulated back to the first column to react with other (P)—α'—A groups of the polymer and thus continue the procedure until the reaction is completed and either the first column is substantially depleted or the second column is substantially loaded.

At this point the end product B—A can be separated and recovered from the second column.

Figure 1:
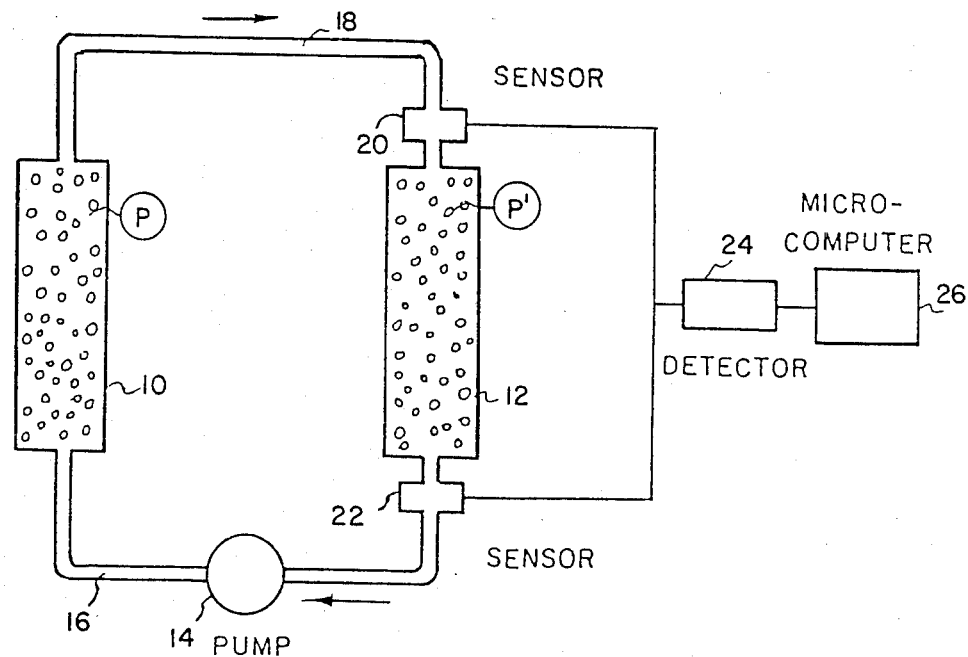
FIG. 1 is a schematic illustration of the apparatus of the present invention.

An apparatus for carrying out such a process is illustrated in FIG. 1. In this apparatus the first polymer-supported reactive species ((P)—α'—A) is packed into column 10 and the second polymer-supported reactive species ((P')—L—B) is packed into column 12. A pump 14 causes the solvent containing the intermediate compounds α and α—A to circulate between the columns 10 and 12 through tubing 16, 18 in the direction of the arrows.

A first sensor 20 is disposed at the entrance to column 12 and a second sensor is disposed at the exit from column 12. These sensors measure the chemical or physical properties of the solution passing therethrough. Sensors 20 and 22 provide their respective outputs to detector 24 which compares the outputs. When the outputs from sensors 20 and 22 are substantially the same, this indicates that no further reaction is taking place in column 12 and thus the reaction in column 12 has been completed. Detector 24 provides a signal to computer 26, such as microcomputer, when such a comparison shows completion of the reaction in column 12 and the microcomputer can then issue appropriate control signals to stop pump 14 and, if desired, automatically begin the next phase of the process, as, for example, separation and recovery of the reaction product from column 12 by means not illustrated. When the sensors 20, 22 are capable of quantitative analysis a continuous direct record of yields may be calculated by computer 26 and the reaction ended whenever a desired yield is obtained.

For carrying out the process of the present invention the reactable polymers (P) and (P') may be the same or different and may comprise any chemically modifiable polymer on which an α' or a B or L moiety, respectively, are attachable. Such polymeric support materials are well known in the art, as for example, is described in Mathur, N. K., et al, "Polymers as Aids in Organic Chemistry", Academic Press 1980, and particularly chapter 2 thereof entitled "Polymeric Support Materials", or Akelah, A., et al, "Application of Functionized Polymers in Organic Synthesis", Chem. Rev., 1981, 81, 557-587, which are hereby incorporated by reference. Any such support materials may be selected depending on the functional group being introduced, as is well known to those skilled in the art. Preferred such polymers are styrene based polymers, silica, polyacrylamide derivatives, cellulose, Sephadex, etc., depending on the particular functional group being introduced.

The compounds B—A synthesizable in accordance with the present invention include all compounds conventionally synthesizable by reaction (I). Such a reaction is common to many different reaction types, including acylation, phosphorylation, phosphitylation, alkylation, hydrogenation, etc. The reaction type may be either electrophilic, nucleophilic or free radical.

For the intermediate reactant α, also known as the "matchmaker", any moiety or ion usable in the conventional reaction scheme (I) can be used. Applicable such compounds or ions will depend on the type of reaction and many examples are provided in the following Examples. It should be understood that, depending on the reaction type, α may be an anion or a cation. When an anion, the cation is usually a hydrogen atom but may also be an alkali metal ion or other suitable cation. When the cation is hydrogen, α is usually shown in the following examples and in the accompanying claims, as the complete compound, including the hydrogen atom (e.g.,

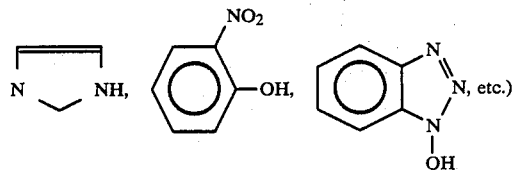

etc.)

When α is a cation, any appropriate anion, such as a halogen, may be used.

For simplicity, the general reaction at the first column is shown as:

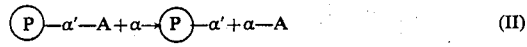   (II)

and the general reaction at the second column is shown as:

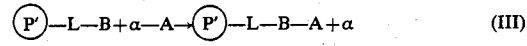   (III)

It should be understood, however, that when an ion replaces A on the polymer in the first column and is replaced by A in the polymer in the second column, they are the same ion, usually a hydrogen, metal or halogen atom, and are not shown in these general reaction schemes so as not to unduly complicate understanding of the present invention.

Sometimes, of course, α is neutral which makes complexes with A and thus leaves no ion on the polymer.

The linking group α' is a group which may be the same as α. The only requirements which must be met in selecting such a group is that it be attachable to (P) by a chemical bond strong enough that it is not detachable from (P) under the reaction conditions. Furthermore, it must be reactable with A to form the compound (P)—α'—A with a bond between α' and A which is disruptable by α. Even if the reaction (II) is reversible such that an equilibrium can be attained, at stable reaction conditions, between the reactants and the reaction products, this represents a sufficiently disruptable bond between α' and A as fresh α is continuously circulated into the column and formed α—A is continuously being removed therefrom. The linking group α', however, is immobile and trapped in the column.

Examples of reactions and reactants usable in the present invention are set forth in the following Examples. A summary of Examples 1-24 is set forth in Table 1.

Among the suitable solvents in which the present reaction may be conducted are anhydrous chloroform, ethanol, ether, acetone, methylene chloride, water, dimethylformamide, acetonitrile, ethyl acetate, tetrahydrofuran, toluene, etc. Any solvent which is a solvent for α and α—A and which does not react with any of the reactants or reaction products can be used.

Figure 2:
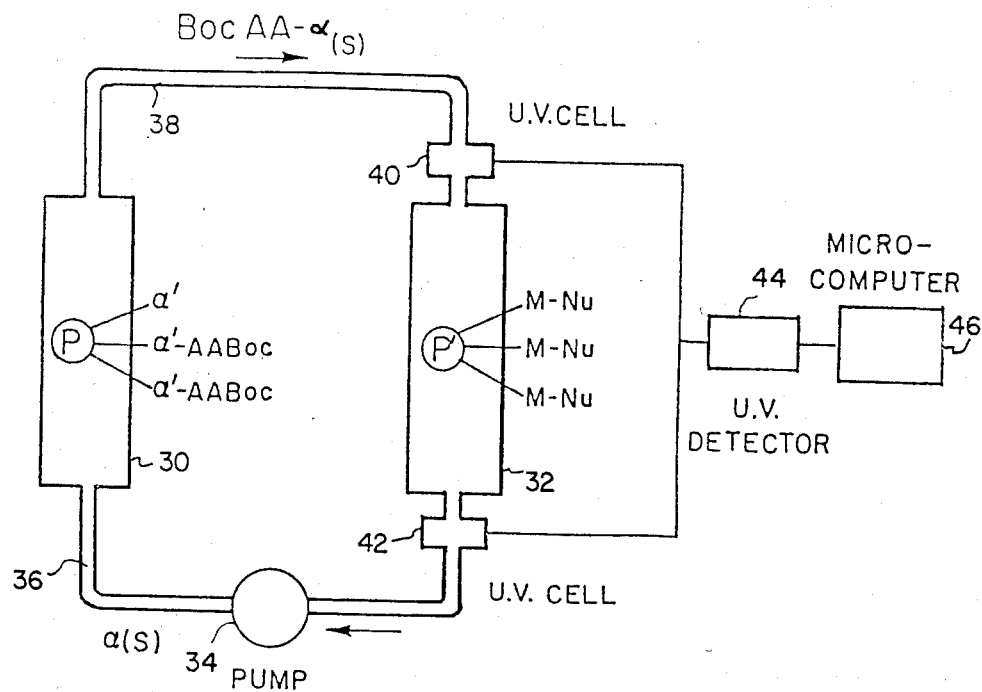
FIG. 2 is a schematic illustration of an apparatus in accordance with the present invention shown in an initial stage of peptide synthesis.
Figure 3:
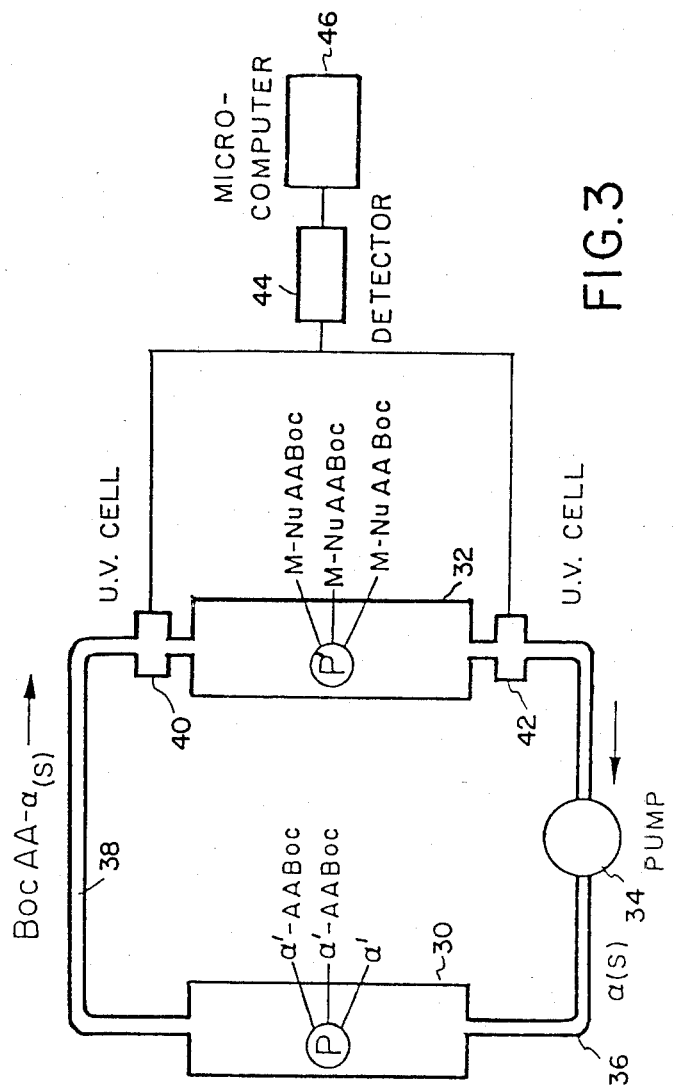
FIG. 3 is a schematic illustration of the apparatus of FIG. 2 in a later stage of peptide synthesis.

The present invention is particularly suitable for the automated production of polypeptides. The general scheme for the synthesis of polypeptides in accordance with the present invention is shown in FIGS. 2 and 3. In the first column 30 is packed a polymeric donor which includes an amino acid which is desired to be transferred to the second column for use as a building block in the formation of the polypeptide. The amino acid is terminated by any conventional N-terminal blocking group such as t-butoxycarbonyl (Boc) or benzoxycarbonyl (Z) as is well known, generally, in polypeptide synthesis. The second column 32 is packed with a polymeric acceptor. The solvent(s), containing the matchmaker α is then pumped by pump 34 through tube 36 into column 30 where α begins to react with some of the amino acid groups (AA), forming BocAA-α. This compound is then circulated through tube 38, past sensor 40, which may suitably be a UV cell, and into column 32. The amino acid there reacts with the polymeric acceptor, regenerating the original matchmaker α which is then recirculated to column 30. As the solution containing BocAA-α, sensed by UV cell 40 at the entrance to column 32, will have different UV characteristics than the solution of α at the exit of the column 32, sensed by UV cell 42, the UV detector 44 and microcomputer 46 will permit the reaction to continue.

Eventually, as shown in FIG. 3, the polymeric acceptor in column 32 will become saturated with amino acid and no further reaction will take place therein. When this happens, the solution leaving column 32 will be identical to the solution entering column 32. The identity of these solutions, as sensed by UV cells 40 and 42, will be detected by detector 44 and microcomputer 46 will then activate the process controls which will cause the synthesis to enter the second phase. In this phase the N-terminal protecting group (Boc as shown in FIGS. 2 and 3) will be removed from the polymer in column 32 and the column 30 will be replaced by a new column 30', not shown, containing a different amino acid which is to be linked to the first amino acid already in place in column 32. The same matchmaker solution is then circulated in the manner discussed above until detector 44 detects completion of this reaction. The Boc protecting group is then again removed from the polymer in column 32 and another polymeric donor substituted bearing the next amino acid to be built onto the polymeric acceptor, which now is a chain of two amino acids. This process is continued until the desired polypeptide is formed on the polymeric support in column 32. It can then be separated from the polymer by conventional techniques to yield the desired polypeptide.

EXAMPLE 1

As the first polymer,

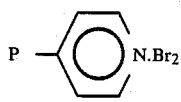

groups may be formed from 2-4% crosslinked polyvinylpyridine according to the methods of U.S. Pat. No. 3,700,610, Okamura, M., et al, *Chem. Abs.* 58-8051 g (1963) or Lloyd, W. G., et al, *J. Appl. Polym. Sci.*, 7, 2025 (1963). For the second polymer,

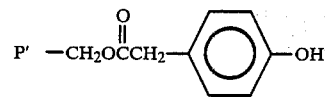

may be prepared by mixing one equivalent of

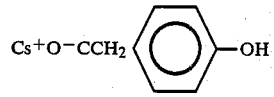

with 1 equivalent of (P')—CH$_2$Cl (Merrifield polymer) in DMF/methanol (1:1) at 50° C. for 6 hours. (P') is 2% crosslinked polystyrene.

The first polymer is placed into a first column and the second polymer into a second column. In a water solvent,

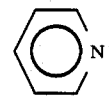

is circulated to the first column. After reacting with the polymer in the first column,

is formed which then circulates to the second column. Upon reaction with the polymer in the second column,

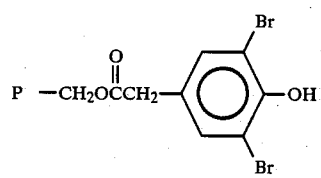

is formed while at the same time regenerating the

for recirculation to the first column.

The cycle is then repeated, all at ambient temperature and pressure. Ultraviolet sensors placed at the entrance and exit of the second column measure the relative presence of

in the solvent. When the concentration of this reagent at the entrance to the column is the same as that at the exit, the second column is fully loaded and the circulation stopped.

The end product,

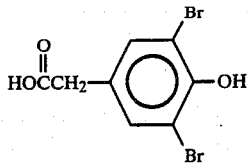

is then cleaved from the polymer by alkaline hyrolysis.

EXAMPLE 2

The process of Example 1 is repeated substituting

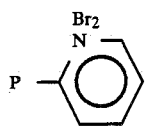

for the polymer in the first column. It may be prepared according to the same known methods as set forth in Example 1. The same product is produced.

EXAMPLE 3

The process of Example 1 is repeated substituting iodine ($I_2$) for bromine ($Br_2$) on the first polymer. The end product obtained is

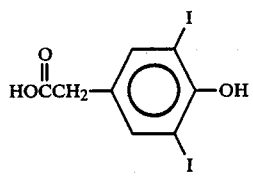

EXAMPLE 4

In the first column is placed

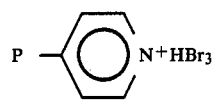

prepared according to Frechet, J., et al, *J. Macromol. Sci. Chem.*, A-11, 507 (1977). In the second column is placed

prepared using

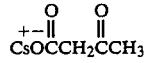

and (P')—$CH_2Cl$ as described in Example 1. In $CH_3OH$ solvent is circulated

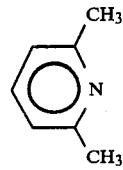

in the manner described in Example 1. The final product,

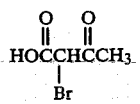

is cleaved from the polymer by HBr/AcOH.

EXAMPLE 5

The procedure of Example 4 is repeated substituting

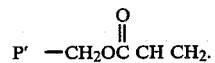

prepared analogously to the method in examples 1 and 4, for the polymer in the second column. The final product

is cleaved as in Example 4.

EXAMPLE 6

The procedure of Example 5 is repeated using

in the first column

in $CH_3OH$ as the circulating matchmaker. The first polymer is prepared by using

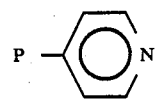

and HF in $CH_3OH$. The final product,

is cleaved as in Examples 4 and 5.

EXAMPLE 7

The procedure of Example 1 is repeated using

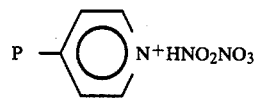

in the first column (prepared by mixing

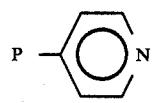

with a solution from HNO$_3$ with P$_2$O$_5$ prepared at 0° C.) and

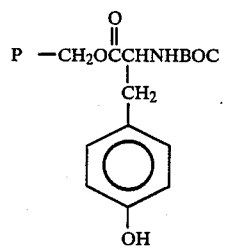

in the second column (prepared analogously to the preparation method detailed in Example 1). As the matchmaker there was circulated

in CH$_2$Cl$_2$. When the reaction was completed, the final product

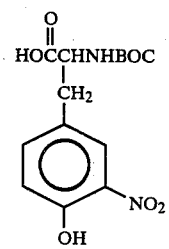

was cleaved from the polymer by alkaline hyrolysis.

EXAMPLE 8

In the first column, there is placed the polymer

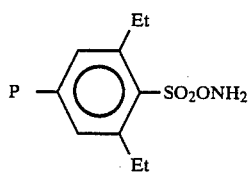

which was prepared by the following reaction scheme:

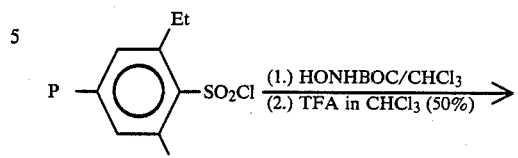

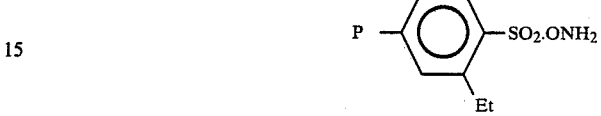

The starting polymer in this reaction scheme was prepared according to Rubinstein, M., *Tetrahedron Letters*, 2881 (1972). In the second column is placed the polymer

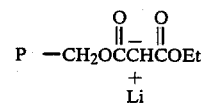

This polymer was prepared using

and (P)—CH$_2$Cl in DMF/methanol (1:1) at 50° C. for 6 hours and then treating the polymer with BuLi. As the matchmaker, there is circulated

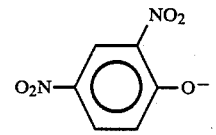

in CH$_2$Cl$_2$. Upon completion of the procedure, circulation is stopped and the final product

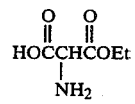

is cleaved from the polymer by HBr/AcOH.

EXAMPLE 9

In the first column is placed

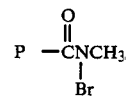

prepared in accordance with the following procedure:

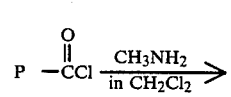

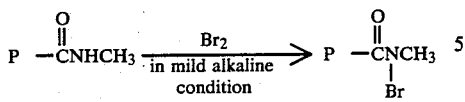

The starting polymer in this procedure was prepared according to Hallensleben, M. L., *Agnew Macromol. Chem.*, 31, 143 (1973). In the second column is placed the same polymer as used in Example 1. As the matchmaker there is circulated

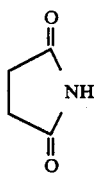

in water. The same final product as in example 1 is cleaved in the manner described therein.

EXAMPLE 10

In the first column is placed

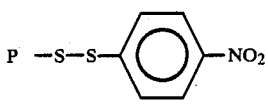

prepared according to *Polymer Chemistry Addition*, volume 20, page 1469–1487 (1982). In the second column is placed

P' —CH$_2$OCCHNHBOC
       |
       CH$_2$
       |
       SH prepared using

C$_5$$^+$OCCHNHBOC
       |
       CH$_2$
       |
       SH and (P')—CH$_2$Cl as described in Example 1. As the matchmaker there is used

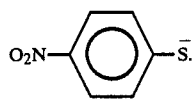

The final product,

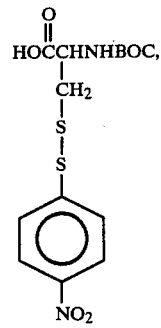

was cleaved from the polymer in the manner described in Example 1.

EXAMPLE 11

In the first column is placed

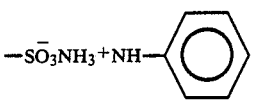

which is prepared by neutralization of (P)SO$_3$H, sulfonated macroporous polystyrene, with excess

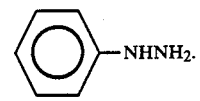

In the second column is placed

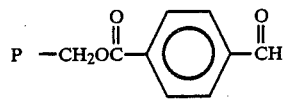

prepared using

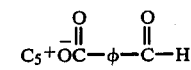

and (P')—CH$_2$Cl
as described for Example 1. As the matchmaker, there is used

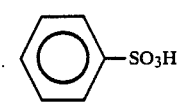

in dioxane. The final product,

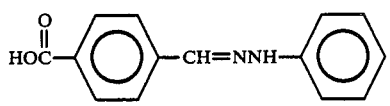

was cleaved by HBr/AOH.

EXAMPLE 12

In the first column there was placed

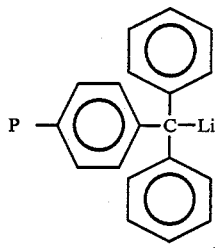

prepared as described in *JACS*, 99, 4165 (1979), (P) being 2% crosslinked polystyrene. In the second column there is placed

which was prepared using

and (P)—CH₂Cl as described in Example 1. The matchmaker was

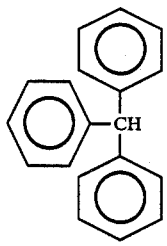

in THF. The reaction product need not be separated from the polymer but the polymer itself is useful as a polymeric reactive species in other processes (for example, one analogous to example 8).

EXAMPLE 13

In the first column is placed the polymer (P)—COOOH prepared according to Fretchet, G. M. G., et al, *Macromolecules*, 8, 130, 1975; Harrison, C. R., et al, *J. Chem. Soc., Perkin Trans.* 1, 605 (1976); *J. Chem. Soc., Chem. Commun.* 1009 (1974). In the second column is placed

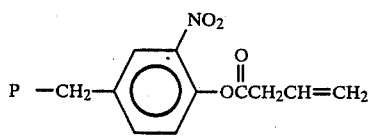

prepared using the symmetric anhydride

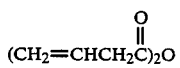

and

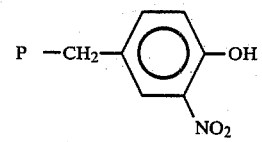

with the addition of pyridine in $CH_2Cl_2$ at 25° C. The matchmaker used is $CH_3COOH$ in dioxane. The final product,

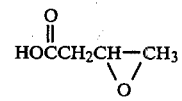

was cleaved from the polymer by hydrolysis in water/dioxane (pH=8).

EXAMPLE 14

In the first column is placed the polymer

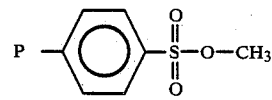

prepared according to the following reaction scheme:

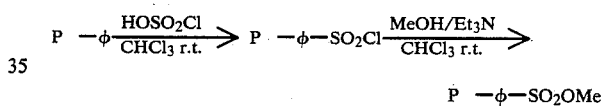

In the second column is placed

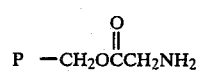

prepared using $C_3{}^+\overline{O}COCH_2NHBOC$ and (P)—CH₂CL in the manner described in Example 1, and then treatment with 50% $TFA/CHC_{13}$ for 15 minutes at room temperature to remove the BOC group. The matchmaker used is $I^-$ in DMF. The final product,

was cleaved from the polymer by alkaline hydrolysis.

EXAMPLE 15

In the first column is placed the polymer

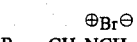
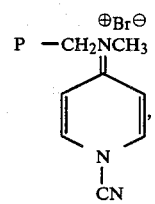

in which Ⓟ is 2% crosslinked polystyrene, prepared in accordance with the following reaction scheme:

P —CH₂Cl $\xrightarrow{\text{CH}_3\text{NH}_2}{\text{CHCl}_3, 25° C.}$

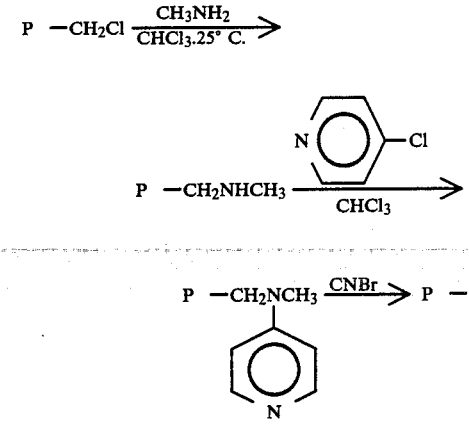

P —CH₂NHCH₃ $\xrightarrow{\text{CHCl}_3}$

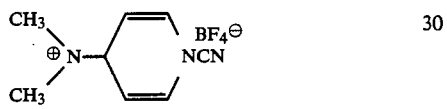

P —CH₂NCH₃ $\xrightarrow{\text{CNBr}}$ P —CH₂⊕NCH₃.

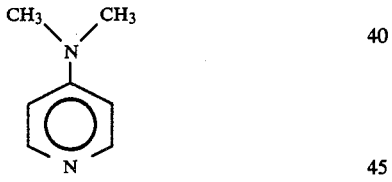

In the second column is placed Ⓟ OH which may be the commercial polymer Sepharose or Sephadex. Reaction of such a polymer with the soluble reagent

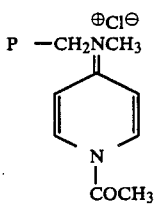

was done by J. Kohn and M. Wilchek in *Febs Letters*, v. 154, No. 1 (1983). The matchmaker used is

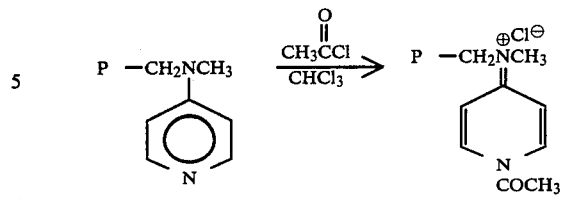

in methanol. After completion of the reaction, the polymer obtained in the second column is Ⓟ—O—CN which may be used per se as a starting product for further reactions.

EXAMPLE 16

In the first column is placed the polymer

prepared according to the procedure described in the scheme below:

This reaction was done in solution. (Hofle, G. et al, *Angew. Chem., Int. Ed. Eng.* 17, 569–583 (1978)). The starting material for this reaction is prepared as described above in Example 15. In the second column is placed

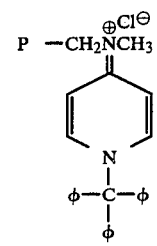

prepared as set forth above in Example 14. The matchmaker used is the same as used in Example 15, although the solvent was changed to chloroform. The final product,

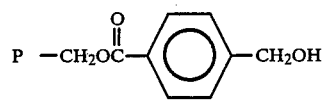

was cleaved from the polymer by alkaline hydrolysis.

EXAMPLE 17

In the first column is placed the polymer

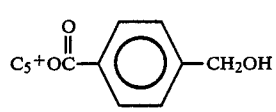

prepared by reacting the same starting polymer as used in Example 16 with trityl chloride in chloroform at 25° C. In the second column is placed

P —CH₂OC(=O)—⌬—CH₂OH which was prepared using

C₅⁺OC(=O)—⌬—CH₂OH and Ⓟ—CH₂CL as described above in Example 1. The matchmaker used was the same as described in Example 15 in CHCl₃. The final product

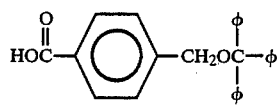

was cleaved from the polymer by alkaline hydrolysis.

EXAMPLE 18

In the first column is placed the polymer

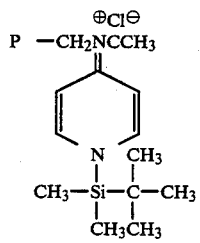

which is prepared in accordance with the following scheme:

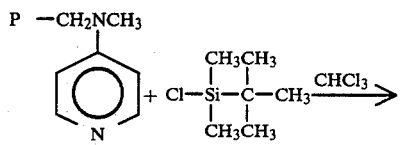

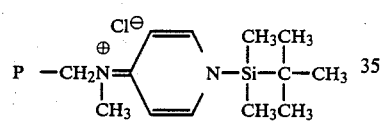

In the second column is placed the same polymer as used in the second column in Example 17. The matchmaker is the same compound and the same solvent as used in Example 17. The final product,

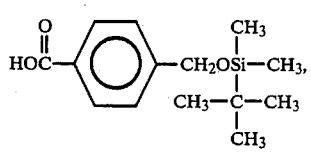

is cleaved from the polymer by alkaline hydrolysis.

EXAMPLE 19

In the first column is placed the polymer

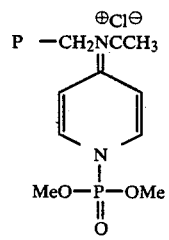

which is prepared by reacting the same starting compound as in Example 15 with

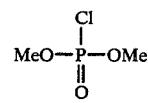

in chloroform. In the second column is the same polymer as used in the second column in Example 17. The matchmaker is

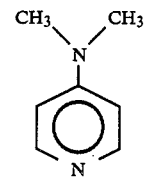

in Et3/CHCl3. The end product,

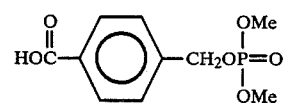

is cleaved from the polymer by alkaline hydrolysis.

EXAMPLE 20

In the first column is placed the polymer

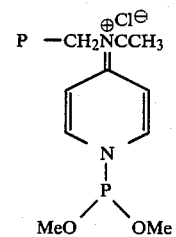

which is prepared by reacting the same starting material as in Example 15 with

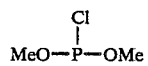

in chloroform. The polymer in the second column and the matchmaker and the solvent are the same as used in Example 19. The end product

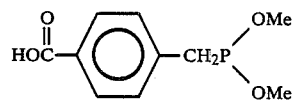

is cleaved from the polymer by alkaline hydrolysis.

EXAMPLE 21

In the first column is placed the polymer

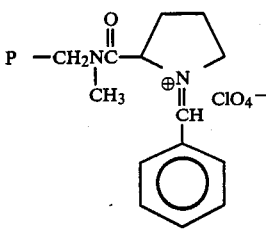

which is prepared according to the following scheme:

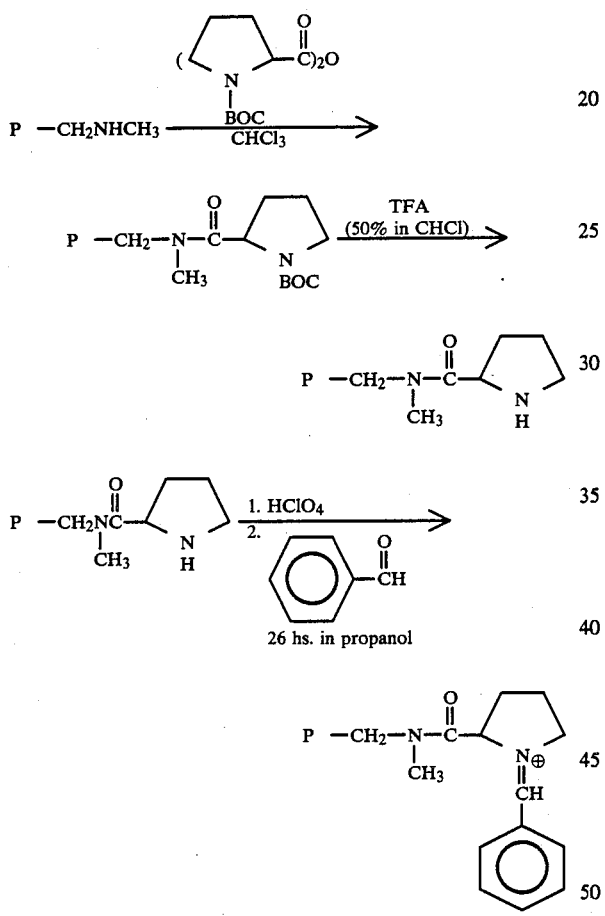

In the second column is placed the polymer

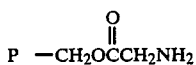

which is the same polymer used in Example 14. The matchmaker is

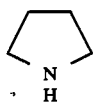

in isopropanol. The final product

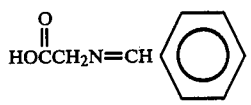

is cleaved from the polymer under mild alkaline conditions. Reactions of this type have been done in solution by Leonard N., et al in *J.O.C.* 28 (1963) 3021.

EXAMPLE 22

This example shows how enkephalin may be synthesized by means of the present invention. Enkephalin is a pentapeptide of the structure Tyr—Gly—Gly—Phe—Leu—OH. It is prepared in the apparatus shown in FIG. 4. In column 50 is placed the first polymeric donor (P)—OPheBoc. This polymer may be prepared by first preparing a symmetrical anhydride (BocPhe)$_2$O according to Weygand, F. et al, *Z. Natureforsch.*, 22b, 1084 (1967). This symmetrical anhydride may be reacted with any polymer (P)—α'—H in which α' is, for example,

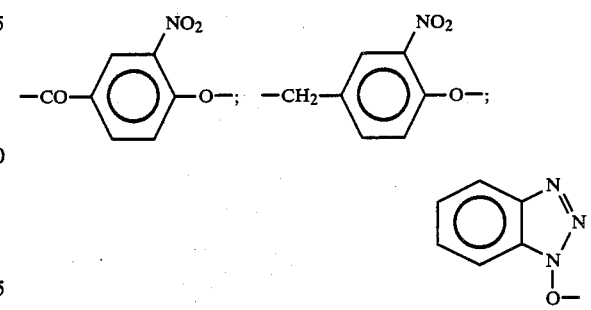

The reaction takes place in the presence of triethylamine or pyridine in a molar ratio of 1:1:3, respectively, as for example, in accordance with the following reaction scheme:

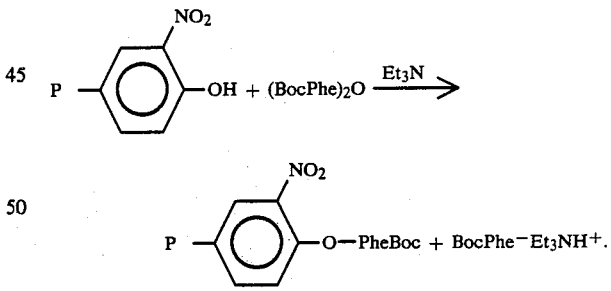

The same starting material can also be prepared by placing chlorosulfonated polystyrene ((P)—SO$_2$Cl) in a first column in apparatus such as that of FIG. 1, and placing (P)—α'H in a second column in which α' is as set forth above. Two equivalents of a triethylammonium carboxylate salt of the N-protected amino acid is then circulated between the columns at −5° to +20° C. for two hours. The carboxylate salts become dehydrated by the action of the P SO$_2$Cl, giving symmetrical anhydrides in high yields. These anhydrides so formed, react in situ with P —α'H to give the desired loaded polymer, (P)—α'—AABoc in which AA is any desired amino acid, such as Phe. The BocAAOH released is again converted to the symmetrical anhydride by the excess of (P)—SO₂Cl present. In both cases loading of between 0.5–1.5 meq protected amino acid per gram of polymeric nitrophenol may be achieved.

The columns 52 and 54 may be loaded with the amino acid reservoir polymers (P)—OGlyBoc and P OTyr (2,6-Dichloro-OBzl)Boc, respectively, by the same reaction scheme merely substituting the appropriate amino acid for Phe.

Column 56, which corresponds to the second column in the simpler examples, is loaded with the polymeric acceptor (P')—LeuNH₂. This polymer may be prepared according to R. B. Merrifield, *J. Amer. Chem. Soc.*, 85, 2149 (1963).

Alternatively it may be prepared by reacting 2 g of 2% crosslinked chloromethylated polystyrene ((P)—CH₂Cl) containing 1 meq/g chloromethyl (CH₂Cl) groups with 2.2 meq of the salt BocLeuO⁻Cs⁺ in dimethyl formamide. The reaction is carried out either by mixing the salt in the polymer, or by putting each one in a separate column and circulating the solvent dimethyl formamide between them for two hours. More than 1.8 meq of BocLeu residue, covalently bound to the polymer, is obtained, with a yield of greater than 90%. The polymer is then treated with 50% TFA (CF₃COOH) in CHCl₃, for 20 minutes and washed with CHCl₃, EtOH/CHCl₃ and CHCl₃. The polymer is then neutralized with a solution of 5% Et₃N in chloroform, and washed with dry CHCl₃ to give the desired polymer, H—Leu—O—CH₂—(P').

The coupling reaction then proceeds in accordance with procedures set forth in Table 2 by setting each of the valves $V_1$ to $V_9$ in accordance with the position in Table 2, and operating the pump 58 as set forth in Table 2. Thus it can be seen, for example, in the first step that reagent 1 (CHCl₃) from inlet 68 is pumped into the system through column 50, then through UV cell 60, column 56, and UV cell 62, and then out of the system at 74.

In step 2, the "matchmaker" imidazole (No. 5 at input 68) is charged for 1.5 minutes, following which valve V₈ is switched in order to cause the imidazole to circulate through column 50, then through UV cell 60, column 56, UV cell 62, and then back to column 50. This continues until the amounts of imidazole as detected by UV cells 60 and 62, are the same, as detected by UV detector 64, which will then signal computer 66 to proceed to the next step of the procedure. In this step, valves V₂ and V₈ are switched, and reagent 1 (CHCl₃) is caused to enter the system in order to wash out column 56. After 4 minutes, the reagent DMF is used to wash the same column.

In the next step, step 8, nitrogen gas is caused to enter through valve 9 through a TFA column 70, and through column 56 in order to remove the Boc group from the polymer. This is then allowed to react for 20 minutes until the Boc group is totally removed. The system is then washed in accordance with steps 8, 9, 10, and 11, and the system is then ready to place the next amino acid in the polypeptide chain for the synthesis of enkephalin. To do this, all of the steps of Table 2 are repeated with valve 2 always being in position 1, and valve 3 being in position 2 for steps 1, 2 and 3. This will permit the matchmaker to circulate between columns 52 and 56.

Thus, at the beginning of this second run through Table 2, column 56 is charged with (P)—CH₂—O—Leu—Phe—H. At the end of the second pass through Table 2, the positions of valves 2 and 3 are switched, and a glycine group will have been added to the chain, so that the polymer in 56 will now be P —CH₂—O—Leu—Phe—Gly—H.

The third time through Table 2 is then repeated in order to add another Gly group, and then the procedure of Table 2 is again repeated but this time having both valves 2 and 3 being at position 1 at all times, and valve 4 being in position 1 at all times except for the first three steps in which it is at position 2. At the end of the fifth step on this fourth time through the table, the polymer in column 56 will be the pentapeptide (P)—CH₂—O—Leu—Phe—Gly—Gly—Tyr(OBzl)—Boc. At this point, before removal of the Boc group, the solvent triethylamine in methanol (not shown) is circulated through the column for 48 hours to give the cleaved product Boc—Tyr(OBzl)—Gly—Gly—Phe—Leu—OCH₃ in almost quantitative yield. The protected peptide enkephalin was identified by amino acid analysis and HPLC, and was identical to an authentic compound prepared by classical synthesis.

Figure 4:
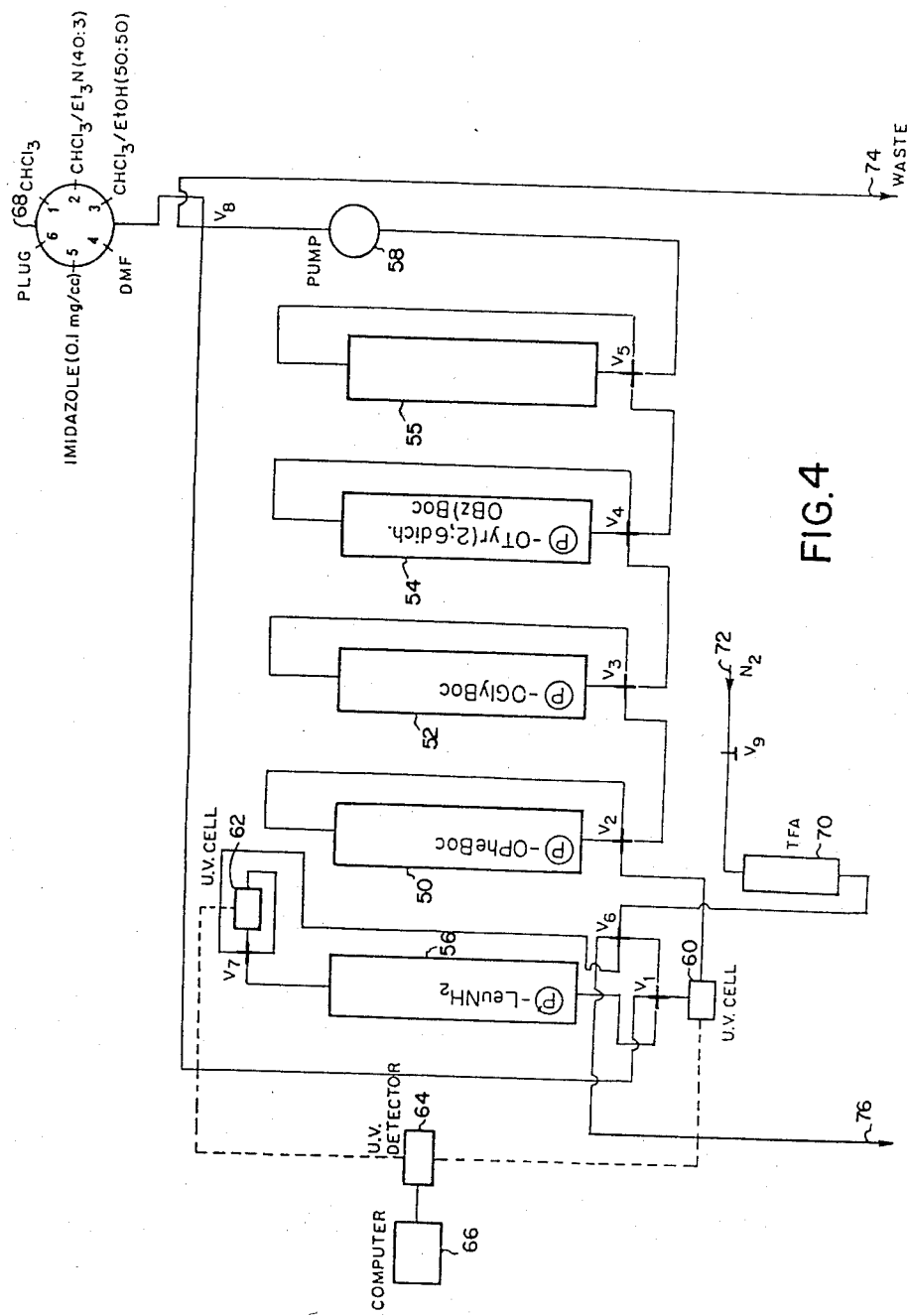
FIG. 4 is a schematic illustration of an apparatus for the synthesis of polypeptides, such as enkephalin.

The device shown in FIG. 4 may be all housed in a single housing with all of the times controlled by the computer 66. By appropriate selection of the polymer columns, any polypeptide can be automatically synthesized with such an apparatus in a manner analogous to the present example.

EXAMPLE 23

In a manner similar to that discussed in Example 22, oligonucleotides can be synthesized in accordance with the method and apparatus of the present invention. This may be accomplished by either phosphitylation or phosphorylation.

In phosphitylation, the first column is loaded with a polymer such as the following:

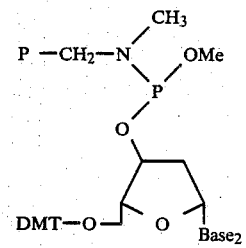

in which base₂ is a protected nucleotide base residue, and DMT is dimethoxytrityl. In the second column is loaded a polymer such as the following:

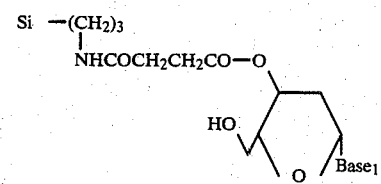

in which the polymer is a silica and Base₁ is a protected nucleotide base residue. The matchmaker compound may be

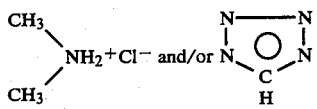

in acetonitrile. At the completion of the reaction, the polymer in the second column will have the formula

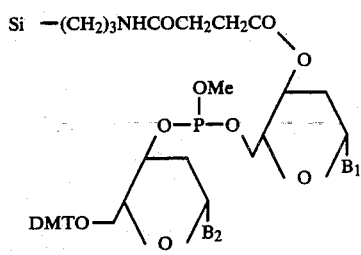

This dinucleotide may be used for further elongation or may be released after oxidation with $I_2$ of the phosphorous residue.

EXAMPLE 24

In phosphorylation reactions, the polymer in the the first column may be:

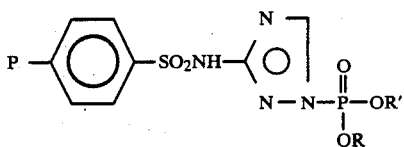

The polymer in the second compound may be the same as that used in Example 23. The matchmaker molecule may be

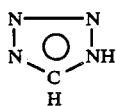

or

in acrylonitrile.

The final product, which is a dinucleotide phosphate triester, may be used for further elongation or cleaved by conventional methods. In the formula given above for the first polymer, R and R' are blocked nucleotide residues.

EXAMPLE 25

A first column is filled with polymeric coupling reagent consisting of poly(3,5-diethylstyrene)sulfonyl chloride, 5% crosslinked, prepared according to Rubinstein, M. et al, *Tetrahedron Letters*, No. 28, pages 2881-2884 (1972). The second column was filled with with a polymeric acceptor comprising a nucleotide-3'-ester prepared according to Plus, R. C. et al, *Nucl. Acid Res.*, vol. 2, page 773, from a polymeric acid chloride (on 0.2% crosslinked polystyrene) and 5'-dimethoxy-trityl thymidine. The 5' protected monomer

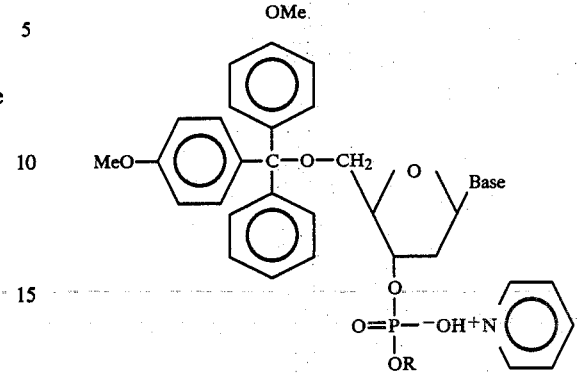

in which R is O-chlorophenyl, and the base is thymine, was circulated in pyridine solution through both the polymeric coupling reagent and the polymeric acceptor polymer beds. After circulation overnight, the polymeric acceptor is washed thoroughly and the dinucleotide cleaved from the polymer with dilute ammonium hydroxide. The product, 5'-dimethoxytrityl-TpT, was identified by high pressure liquid chromatography. Yields ranged from 10% to 80%.

It should be understood that the above processes are applicable to a wide range of reactions. For example, in acylation reactions, in which A is

$a'$ may be selected from a broad range of moieties such as

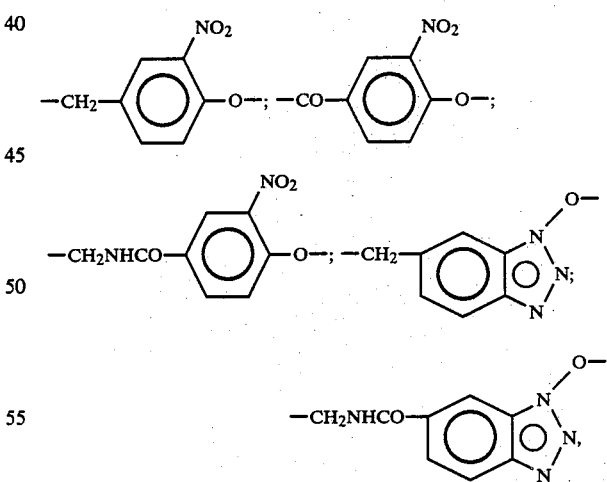

and $a$ may be any of

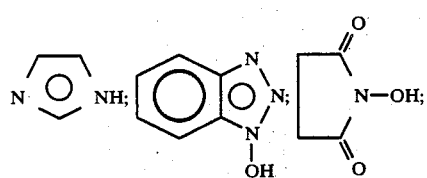

-continued

CH₃CH₂SH/Et₃N, etc. In the second column, B may be any amino acid or peptide or other nucleophile. It should be understood, however, that α', α, A and B are not limited by the above examples, but only by the general functional definitions previously provided and as set forth in the attached claims.

Advantages of the method of the present invention, particularly for peptide synthesis, include the fact that the excess of α—A, e.g. acyl imidazole, is small compared to conventional syntheses. An excess of 30% meq may be used as compared to 100-500% in conventional reactions. Furthermore, the excess of α—A (the 30% meq) can be recovered by passing through virgin ⓟ—α'.

An additional advantage is the fact that there is a great economizing on solvents. By adding two volumes of solvent, one can remove 70%-95% of excess compounds in solution. By conventional processes, to get rid of the final 30-35%, one needs sometimes 3-30 volumes of solvent such as in the Merrifield approach. In the present case, circulating the solvent through a trap, such as a polymeric type, saves much solvent. The trap absorbs the undesired reagents from the solvent. For example, to remove excess TFA after cleaving the Boc group, in the step of neutralization, by circulating the solvent through a basic resin, one removes most of the TFA as a polymeric salt:

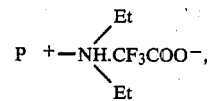

By saving on solvent, one also achieves the advantage of diminishing pollution, as there are less used solvents to dump.

The sensors used at the entrance and exits of the second column of the present invention may be calibrated to quantitate the concentration of α—A. Therefore, the difference in concentration in the two sensors multiplied by the volume of solvent reflects the amount of reagent attached to ⓟ'—B to form ⓟ'—BA. Therefore, one can obtain a direct record of yields. This can be done continuously.

It will be obvious to those skilled in the art that various changes may be made without departing from the scope of the invention and the invention is not to be considered limited to what is shown in the drawings and described in the specification.

TABLE 1

| Example No. | ⓟ - α | ⓟ α-A | α |
|---|---|---|---|
| 1 | 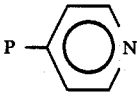 | 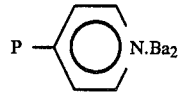 |  in H₂O |
| 2 | 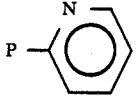 | 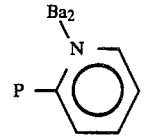 |  in H₂O |
| 3 | 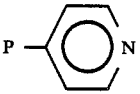 | 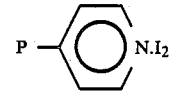 |  in H₂O |
| 4 | 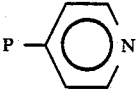 |  | 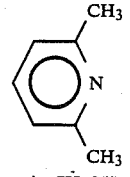 in CH₃OH |
| 5 | 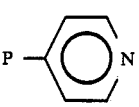 |  | 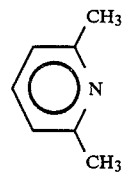 in CH₃OH |

TABLE 1-continued
| | | | |
|---|---|---|---|
| 6 | 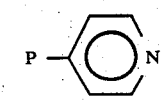 |  | <br>in CH$_3$OH |
| 7 | 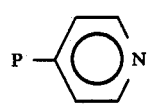 | 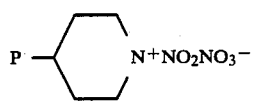 | <br>in CH$_3$Cl$_2$ |
| 8 | 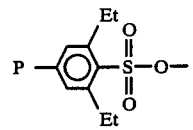 | 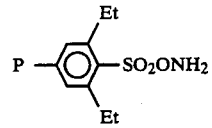 | 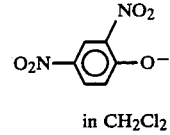<br>in CH$_2$Cl$_2$ |
| 9 | 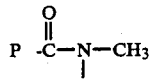 | 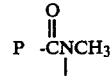 | <br>in H$_2$O |
| 10 |  | 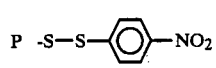 | 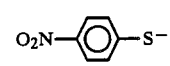<br>in CH$_3$Cl$_2$ |
| 11 |  | 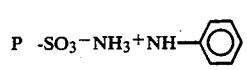 | 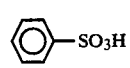<br>in dioxane |
| 12 | 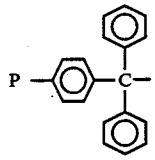 | 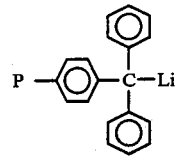 | |
| 13 |  |  | <br>in dioxane |
| 14 | 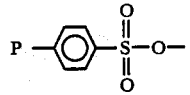 | 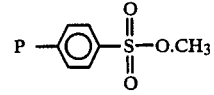 | I$^-$<br>in OnF |
| 15 | 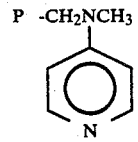 | 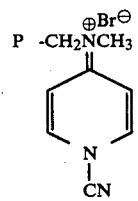 | 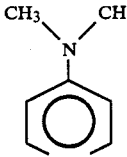 |

TABLE 1-continued
| | | | |
|---|---|---|---|
| 16 | " | 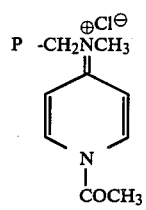 | " |
| 17. | 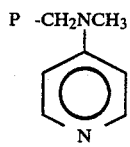 | 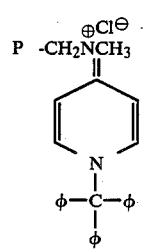 | 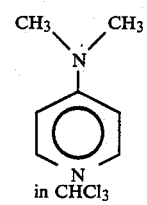 in CHCl₃ |
| 18 | " | 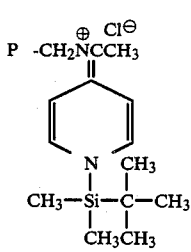 | 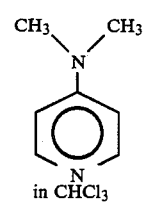 in CHCl₃ |
| 19 | " | 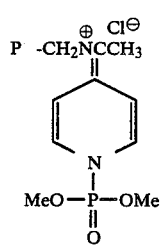 | 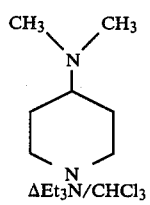 ΔEt₃N/CHCl₃ |
| 20 | " | 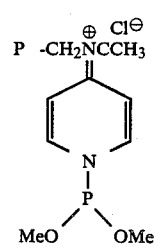 | 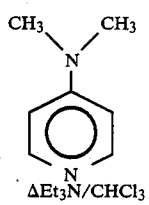 ΔEt₃N/CHCl₃ |
| 21 | 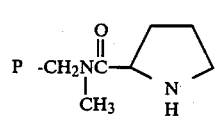 | 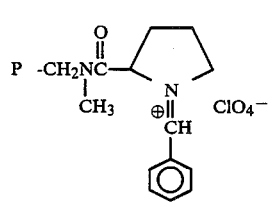 | 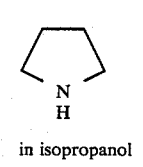 in isopropanol |
| 22(a) | 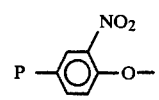 | 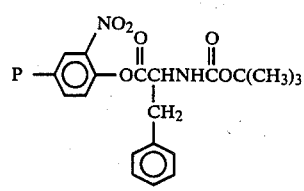 | 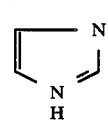 in CHCl₃ |

TABLE 1-continued
| Example No. | P -β | P -βA | βA |
|---|---|---|---|
| 22(b) | 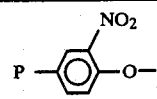 | 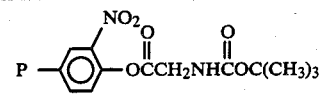 | " |
| 23 |  | 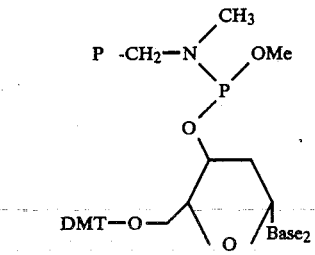 | 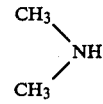 |
| 24 | 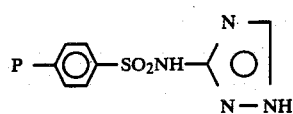 | 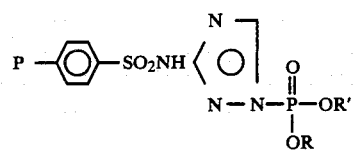 | 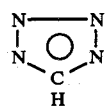 |
| 1 | 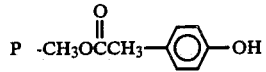 | 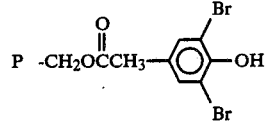 | 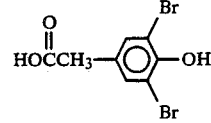 |
| 2 | 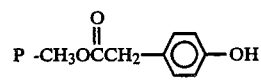 | 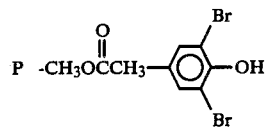 | " |
| 3 | 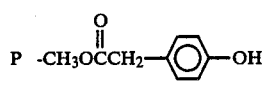 | 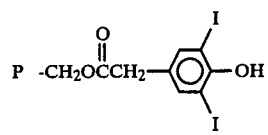 | 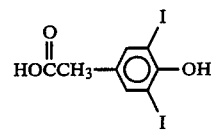 |
| 4 |  | 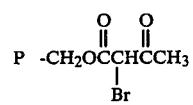 | 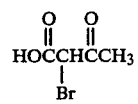 |
| 5 |  |  |  |
| 6 | " | 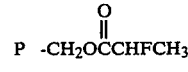 |  |
| 7 | 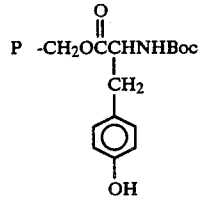 | 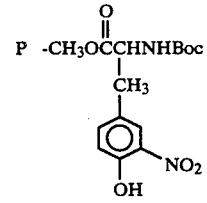 | 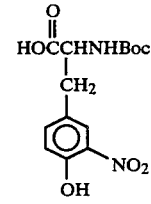 |
| 8 | 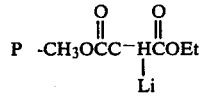 | 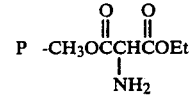 | 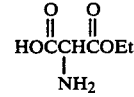 |

TABLE 1-continued

| | | | |
|---|---|---|---|
| 9 | P-CH₂OCCH₃—⟨⟩—OH | P-CH₃OCCH₃—⟨Br⟩—OH(Br) | HOCCH₃—⟨Br⟩—OH(Br) |
| 10 | P-CH₂OCCHNHBoc, CH₃, SH | P-CH₂OCCHNHBoc, CH₃, S-S-⟨⟩-NO₂ | HOCCHNHBoc, CH₃, S-S-⟨⟩-NO₂ |
| 11 | P-CH₂OC-⟨⟩-CH=O | P-CH₂OC-⟨⟩-CH=N—NH-⟨⟩ | HOC-⟨⟩-CH=NNH-⟨⟩ |
| 12 | P-CH₂OCCH₃CH₃ | P-CH₂OCCHCH₃, Li | The polymer was used for further reactions |
| 13 | P-CH₂-⟨NO₂⟩-OCCH₂CH=CH₂ | P-CH₂-⟨NO₂⟩-OCCH₂CH—CH₂, O | HOCCH₂CH—CH₃, O |
| 14 | P-CH₂OCCH₃NH₂ | P-CH₂OCCH₂NHCH₃ | HOCCH₂NHCH₃ |
| 15 | P-OH | P-OCN | The polymer was used for further reactions. |
| 16 | P-CH₂OCCH₂NH₂ | P-CH₂OCCH₃NHCCH₃ | HOCCH₂NHCCH₃ |
| 17 | P-CH₂OC-⟨⟩-CH₃OH | P CH₂OC-⟨⟩-CH₂OC-φ, φ | HOC-⟨⟩-CH₂OC-φ, φ |
| 18 | " | P-CH₂OC-⟨⟩-CH₂OSi(CH₃)₂-C(CH₃)₃ | HOC-⟨⟩-CH₂OSi(CH₃)₂-C(CH₃)₃ |
| 19 | " | P-CH₂OC-⟨⟩-CH₂O-P(=O)(OMe)₂ | HOC-⟨⟩-CH₂OP(=O)(OMe)₂ |
| 20 | " | P-CH₂OC-⟨⟩-CH₂OP(OMe)₂, OMe | HOC-⟨⟩-CH₂OP(OMe)₂, OMe |
| 21 | P-CH₂OCCH₂NH₂ | P-CH₂OCCH₂N=CH-⟨⟩ | HOCCH₂N=CH-⟨⟩ |

TABLE 1-continued

| | | | |
|---|---|---|---|
| 22(a) | P—CH$_2$OCCHNH$_2$ with side chain CH$_2$CH(CH$_3$)$_2$ (leucine) | P—CH$_2$OCCHNHCCHNHCOC(CH$_2$)$_3$ with side chains CH$_2$CH(CH$_3$)$_2$ and (CH$_2$)$_3$—Ph | The Polymer was used for further reactions |
| 22(b) | P—CH$_2$OCCHNHCCHNH$_2$ with side chains CH$_2$CH(CH$_3$)$_2$ and CH$_2$—Ph | P—CH$_2$OCCHNHCCHNHCCH$_2$NHBoc with side chains CH$_2$CH(CH$_3$)$_2$ and CH$_2$—Ph | The Polymer was used for further reactions |
| 23 | Si—(CH$_2$)$_3$NHCOCH$_2$CH$_2$CO—O—[sugar with HO and B$_1$] | Si—(CH$_2$)$_3$NHCOCH$_2$CH$_2$CO—[sugar with B$_1$] linked via O—P(OMe)—O to DMTO—[sugar with B$_2$] | The Polymer was used for further reactions |
| 24 | " | Si—(CH$_2$)$_3$NHCOCH$_2$CH$_2$CO—[sugar with B$_1$] with R'O—PO(OR)—O— | The Polymer was used for further reactions |

TABLE

| STEP | S | V$_9$ | V$_8$ | V$_7$ | V$_6$ | V$_5$ | V$_4$ | V$_3$ | V$_2$ | V$_1$ | Valves/operation | time | rate of pump cc/min |
|---|---|---|---|---|---|---|---|---|---|---|---|---|---|
| 1 | 1 | off | 2* | 2 | 1** | 1 | 1 | 1 | 2 | 2 | wash | 5 min | 4 |
| 2 | 5 | off | 2 | 2 | 1 | 1 | 1 | 1 | 2 | 2 | addition of imidazole | 1.5 min | 4 |
| 3 | 6 | off | 1 | 2 | 1 | 1 | 1 | 1 | 2 | 2 | coupling | ΔC = 0~24 hr | 4 |
| 4 | 1 | off | 2 | 2 | 1 | 1 | 1 | 1 | 1 | 2 | wash | 4 min | 4 |
| 5 | 4 | off | 2 | 2 | 1 | 1 | 1 | 1 | 1 | 2 | wash | 2.5 min | 4 |
| 6 | 6 | on | 1 | 1 | 1 | 1 | 1 | 1 | 1 | 1 | removal of BOC group | 1 sec | 0 |
| 7 | 6 | off | 1 | 1 | 1 | 1 | 1 | 1 | 1 | 1 | removal of BOC group | 20 min | 0 |
| 8 | 1 | off | 2 | 1 | 2 | 1 | 1 | 1 | 1 | 1 | wash | 6 min | 4 |
| 9 | 2 | off | 2 | 2 | 2 | 1 | 1 | 1 | 1 | 1 | " | 6 min | 4 |
| 10 | 3 | off | 2 | 2 | 2 | 1 | 1 | 1 | 1 | 1 | " | 6 min | 4 |
| 11 | 1 | off | 2 | 2 | 2 | 1 | 1 | 1 | 1 | 1 | " | 6 min | 4 |

*Valve position 1 is 
**Valve position 2 is

What is claimed is:

1. In the method for synthesizing an organic compound B—A synthesizable by the reaction scheme $$B + \alpha\text{—}A \rightarrow B\text{—}A + \alpha \qquad (I)$$

comprising reacting B with the compound α—A under conditions sufficient to permit said reaction, to thereby yield α and the compound B—A, all of A, B, α—A and α being selected to permit said reaction (I) to proceed, the improvement by which said reaction (I) may proceed such that compound B—A is produced and recovered selectively and at high yield with excellent economy of reactants, comprising:

binding the reactant A to a first chemically modifiable polymeric support P by means of a functional group α', which may be the same as α, said first polymeric support and α' being selected with respect to any given set of reactants capable of reacting according to reaction (I) such that α' is attachable to said first polymeric support and, after being attached to said first polymeric support, is reactable with A to form the compound (P)—α'—A, with bonds between α' and said first polymeric support and between α' and A which are of sufficient strength to permit A to detach from (P)—α'—A when (P)—α'—A is reacted with α under reaction conditions sufficient to form α—A and to prevent detachment of α' from said first polymer support under the same reaction conditions;

binding the reactant B to a second chemically modifiable polymeric support (P'), said second polymeric support being capable of reacting with B to form (P')—B with a bond between said second polymeric support and B sufficiently strong to prevent detachment of B under reaction conditions under which said reaction scheme (I) may proceed to form (P')—B—A;

placing said first polymeric support in a first reaction zone having an entrance and a separate exit;

placing said second polymeric support in a second reaction zone having an entrance and a separate exit;

feeding α, in a liquid medium which does not interfere with any of the reactions, to the entrance of the first reaction zone, and causing the liquid medium carrying α to contact said first polymeric support having α'—A bound thereto, under reaction conditions sufficient to permit the following reaction to take place:

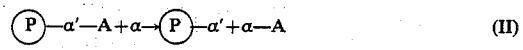
(II)

removing the liquid medium which has contacted the first polymeric support through the exit of the first reaction zone;

feeding the liquid medium removed from the exit of the first reaction zone to the entrance of the second reaction zone and causing the liquid medium to contact said second polymeric support having B bound thereto, under reaction conditions sufficient to permit the following reaction to take place:

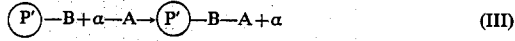
(III)

removing the liquid medium which has contacted the second polymer support through the exit of the second reaction zone;

repeating said feeding and removing steps, using the liquid medium removed from the exit of the second reaction zone as the source of α in reaction (II), thereby circulating the liquid medium between the two reaction zones, until a desired amount of (P')—B—A is produced;

cleaving B—A from said second polymeric support; and recovering B—A.

2. A method in accordance with claim 1, further including the steps of sensing the parameters of a physical or chemical property of the material being fed to the entrance of the second reaction zone and sensing the parameters of a physical or chemical property of the material being removed through the exit of the second reaction zone, wherein the property being sensed at the exit of the second reaction zone is the same as the property being sensed at the entrance to the second reaction zone.

3. A method in accordance with claim 2, wherein said repeating step is continued until a comparison of the parameters sensed with respect to the material at the exit of the second reaction zone with the parameters sensed at the entrance to the second reaction zone yields predetermined results indicating that a desired amount of (P')—B—A has been produced.

4. A method in accordance with claim 1, wherein the said first and second reaction zones comprise columns containing said first and second polymeric supports, respectively, with the entrances and exits to said reaction zones being at opposite ends of the respective columns.

5. A method in accordance with claim 4, wherein the exit of said reaction column is connected to the entrance of said second reaction column, and the exit of said second reaction column is connected to the entrance of said first reaction column, and the solvent is pumped to circulate continuously between said columns until said repeating step is completed.

6. A method in accordance with claim 2, wherein said repeating step is continued until a comparison of the parameters sensed with respect to the material at the exit of said second reaction zone with the parameters sensed with respect to the material at the entrance to said second reaction zone are substantially the same, indicative of substantial completion of the reactions.

7. A method in accordance with claim 1, wherein A and B are amino acids, dipeptides or oligopeptides, and B—A is a dipeptide or oligopeptide.

8. A method in accordance with claim 1, wherein A is an amino acid terminated by an N-terminal blocking group, and B is an amino acid.

9. A method in accordance with claim 8, further including the steps of, prior to said cleaving step:

placing a third polymeric support in a third reaction zone having an entrance and a separate exit, said third polymeric support having an amino acid (A²) terminated by an N-terminal blocking group bound thereto by means of a functional group α' which may be the same or different from the α' used with said first polymeric support;

feeding the α-containing liquid medium used with respect to the first polymeric support to the entrance of the third reaction zone, and causing the liquid medium to contact the third polymeric support under reaction conditions sufficient to permit the following reaction to take place:

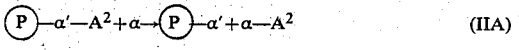
(IIA)

removing the liquid medium which has contacted the third polymeric support through the exit of the third reaction zone;

feeding the liquid medium removed from the exit of the third reaction zone to the entrance of the second reaction zone and causing the liquid medium to contact the second polymeric support under reaction conditions sufficient to permit the following reaction to take place:

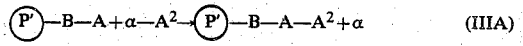
(IIIA)

removing the liquid medium which has contacted the second polymer support through the exit of the second reaction zone; and continuing to circulate liquid medium between said third and second reaction zones until a desired amount of (P')—B—A—A² is produced.

10. A method in accordance with claim 1, wherein A is a nucleotide.

11. A method in accordance with claim 1, wherein reaction (I) is an acylation reaction.

12. A method in accordance with claim 1, wherein reaction (I) is a phosphorylation reaction.

13. A method in accordance with claim 1, wherein reaction (I) is a phosphatylation reaction.

14. A method in accordance with claim 1, wherein reaction (I) is an alkylation reaction.

15. A method in accordance with claim 1, wherein reaction (I) is a hydrogenation reaction.

16. A method in accordance with claim 1, wherein reaction (I) is a halogenation reaction.

17. A method in accordance with claim 1, wherein said first and second polymeric supports comprise styrene based polymers, silica based polymers, polyacrylamine derivatives, or cellulose based polymers.

18. A method in accordance with claim 1, wherein α is selected from the group consisting of:

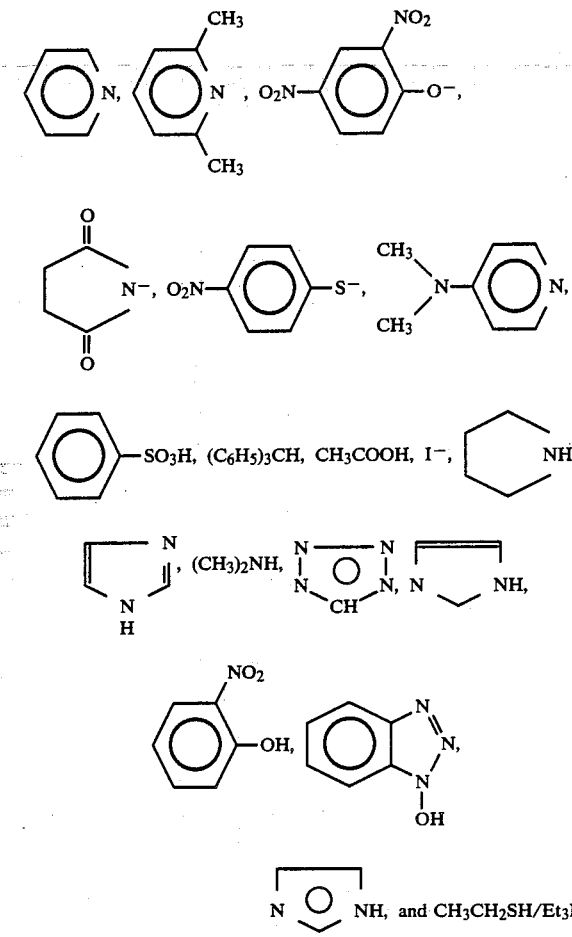

19. A method in accordance with claim 1, wherein α′ is selected from the group consisting of:

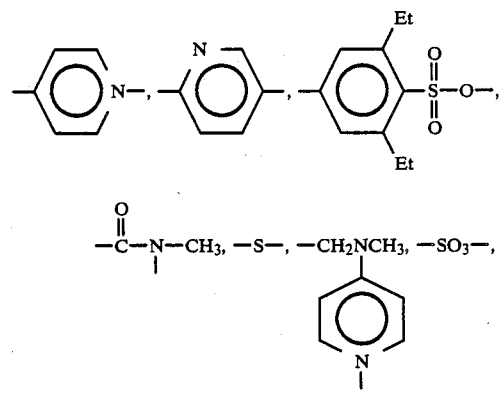

-continued

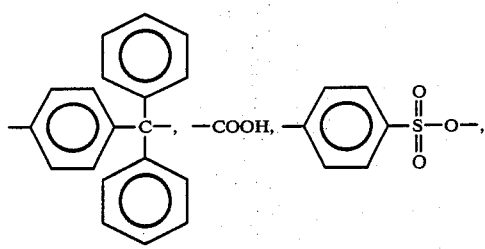

20. A method in accordance with claim 1, wherein A is a protected amino acid or nucleotide, and further including the steps of, after said repeating step and prior to said cleaving step, removing the protecting group on the formed second polymeric support and repeating the entire process using a new first polymeric support in which A is another protected amino acid or nucleotide, which maybe the same as or different from the protected amino acid or nucleotide of the previous first polymeric support, to add another amino acid or nucleotide to the chain on the second polymeric support.

21. A method in accordance with claim 1, wherein said liquid medium comprises a solvent which is a solvent for α and α-A and which does not react with any of the reactants or reaction products.

22. A method in accordance with claim 1, wherein said solvent is selected from the group consisting of chloroform, ethanol, ether, acetone, methylene chloride, water, dimethylformamide, acetonitrile, ethyl acetate, tetrahydrofuran, and toluene.

23. In the method for synthesizing an organic compound B—A synthesizable by the reaction scheme $$B + \alpha\text{—}A \rightarrow B\text{—}A + \alpha \qquad (I)$$

comprising reacting B with the compound α—A under conditions sufficient to permit said reaction, to thereby yield α and the compound B—A, all of A, B, α—A and α being selected to permit said reaction (I) to proceed, the improvement by which said reaction (I) may proceed such that compound B-A is produced and recovered selectively and at high yield with excellent economy of reactants, comprising:

binding the reactant A to a first chemically modifiable polymeric support (P) by means of a functional group $\alpha'$, which may be the same as $\alpha$, said first polymeric support and $\alpha'$ being selected with respect to any given set of reactants capable of reacting according to reaction (I) such that $\alpha'$ is attachable to said first polymeric support and, after being attached to said first polymeric support, is reactable with A to form the compound (P)—$\alpha'$—A, with bonds between $\alpha'$ and said first polymeric support and between $\alpha'$ and A which are of sufficient strength to permit A to detach from (P)—$\alpha'$—A when (P)—$\alpha'$—A is reacted with $\alpha$ under reaction conditions sufficient to form $\alpha$—A and to prevent detachment of $\alpha'$ from said first polymer support under the same reaction conditions;

binding the reactant B to a second chemically modifiable polymeric support P', said second polymeric support being capable of reacting with B to form (P')—B with a bond between said second polymeric support and B sufficiently strong to prevent detachment of B under reaction conditions under which said reaction scheme (I) may proceed to form (P')—B—A;

feeding $\alpha$, in a liquid medium which does not interfere with any of the reactions, to contact with said first polymeric support having $\alpha'$-bound thereto, under reaction conditions sufficient to permit the following reaction to take place:

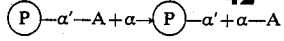

$$\text{(P)}-\alpha'-A+\alpha \rightarrow \text{(P)}-\alpha'+\alpha-A \qquad \text{(II)}$$

feeding the liquid medium which has contacted said first polymeric support to contact with said second polymeric support having B bound thereto, under reaction conditions sufficient to permit the following reaction to take place:

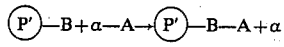

$$\text{(P')}-B+\alpha-A \rightarrow \text{(P')}-B-A+\alpha \qquad \text{(III)}$$

sensing the parameters of a physical or chemical property of the liquid medium being fed to said second polymeric support;

sensing the parameters of a physical or chemical property of the liquid medium which has contacted said second polymeric support, the property sensed being the same as the property being sensed with respect to the liquid medium being fed to said second polymeric support;

repeating said feeding and sensing steps, using the liquid medium which has contacted said second polymeric support as the source of $\alpha$ in reaction (II), thereby circulating the liquid medium between the two polymeric supports, until a comparison of the parameters sensed with respect to the liquid medium which has contacted said second polymeric support with the parameters sensed with respect to the liquid medium which is being fed to said second polymeric support yields predetermined results indicating that a desired amount of (P')—B—A has been produced;

cleaving B—A from said second polymeric support; and recovering B—A.

* * * * *